United States Patent [19]

Kurwa

[11] Patent Number: 4,568,157
[45] Date of Patent: Feb. 4, 1986

[54] GONIOTOMY LENS

[75] Inventor: Badrudin Kurwa, Galveston, Tex.

[73] Assignee: Board of Regents, The University of Texas System, Austin, Tex.

[21] Appl. No.: 630,320

[22] Filed: Jul. 11, 1984

[51] Int. Cl.[4] ............................ A61B 3/00; G02C 7/04
[52] U.S. Cl. .................................. 351/160 R; 351/219
[58] Field of Search ............... 351/160 R, 219, 160 H, 351/161, 162

[56] References Cited

U.S. PATENT DOCUMENTS

| | | | |
|---|---|---|---|
| 3,820,879 | 6/1974 | Frisen | 351/219 |
| 4,033,679 | 7/1977 | Sussman | 351/219 |
| 4,067,646 | 1/1978 | Nohda | 351/219 |
| 4,134,647 | 1/1979 | Ramos-Caldera | 351/219 |
| 4,378,147 | 3/1983 | Fujita | 351/219 |
| 4,439,026 | 3/1984 | Wilms | 351/219 |

Primary Examiner—John K. Corbin
Assistant Examiner—Scott J. Sugarman
Attorney, Agent, or Firm—Arnold, White & Durkee

[57] ABSTRACT

A goniotomy lens includes a truncated generally pyramidal body having four reflective sides, a concave smaller end face and an angled larger upper end face. The angled upper end face permits a standard operating microscope of be utilized since light produced by the microscope is reflected off-axis from the surface to minimize glare. The smaller end face has a curvature of approximately 43 diopters in order to sealing mate with the human eye. The reflective sides of the lens enable the angle of the anterior chamber to be viewed during a goniotomy. The ratio of the height of lens to the width of its base is advantageously less than 2 and most advantageously approximately 1.

11 Claims, 3 Drawing Figures

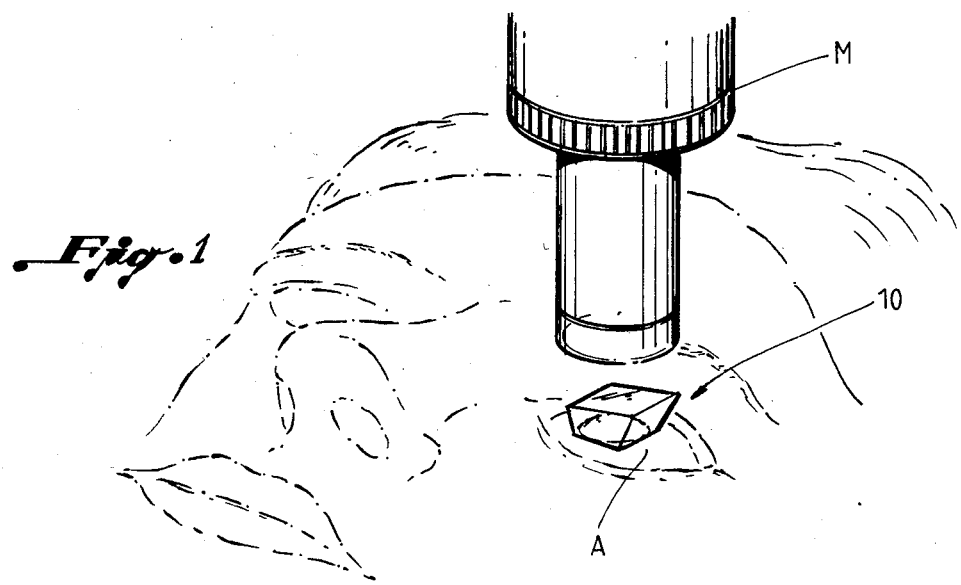
*Fig. 1*
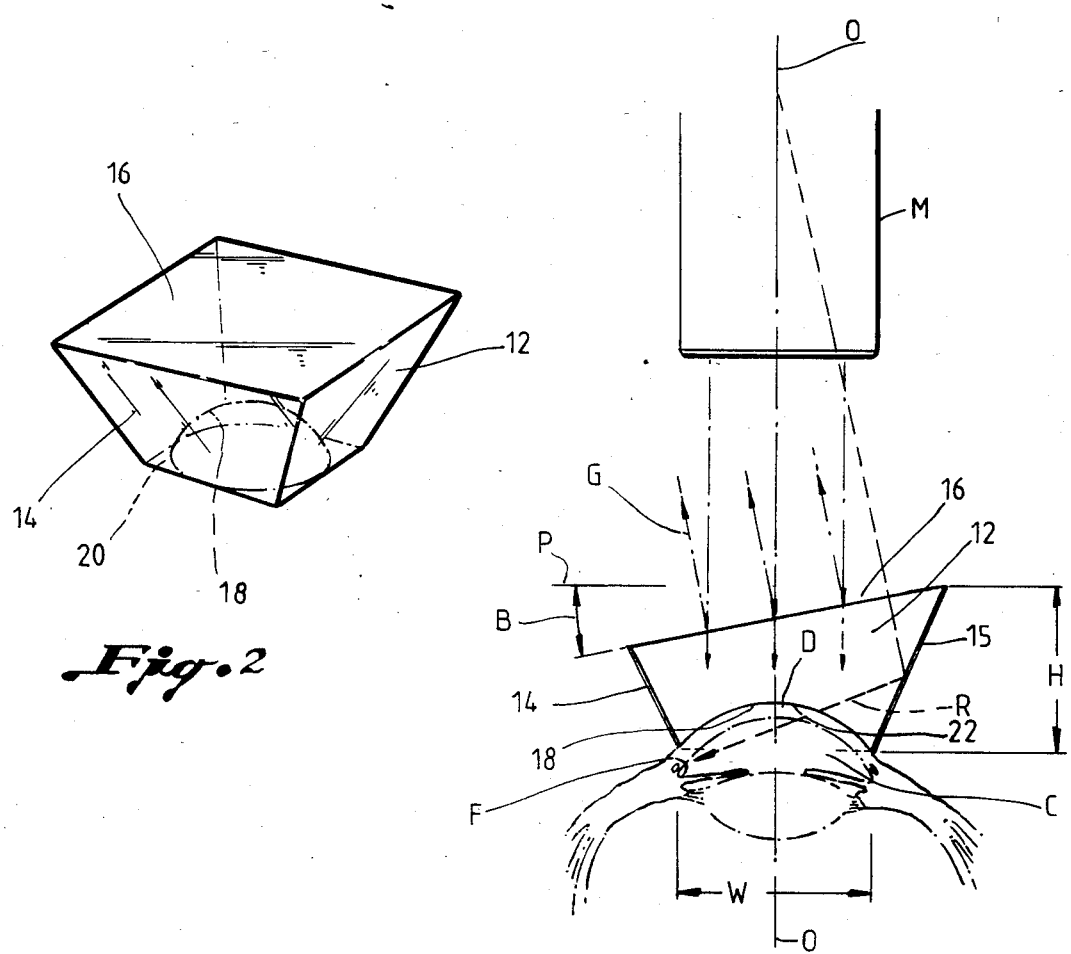
*Fig. 2*
*Fig. 3*

GONIOTOMY LENS

BACKGROUND OF THE INVENTION

1. Field of the Invention

This invention relates generally to gonioscopes and particularly to a lens suitable for use in performing a goniotomy.

2. Brief Description of the Background Art

A goniotomy is the surgical opening of Schlemm's canal (sinus venosus) by way of the angle of the anterior chamber of the eye. This procedure may be necessary in the treatment of congenital glaucoma. The surgical procedure requires an incision at the limbus which is located at the juncture of a cornea and the sclera. The area within the eye which must be viewed in a goniotomy has to be viewed at an angle of approximately 48° from the horizontal plane including the prone patient. Thus, the surgeon is unable to sit as close to the head of the patient as a surgeon would otherwise prefer. In addition the surgeon must position himself or herself at arms length and stoop down to get into the necessary viewing axis. This causes the surgeon to lose magnification and makes the surgeon unstable for fine surgical procedures.

Because of the need for high precision in the surgical procedure, it would be highly desirable to use a standard opthomologist's operating microscope. However, operating microscopes, designed for a vertical or near vertical, slightly angulated viewing, cannot focus on the eye at the 48° angle required to view the angle through a direct lens. Up to now the procedure is performed with spectacle magnifiers or hand held magnifiers which are cumbersome and give only limited magnification with difficult focusing.

U.S. Pat. No. 4,033,679 to Sussman discloses a gonioscope which is useful for viewing the angle of the anterior chamber. While the design disclosed is suitable for its intended purpose, viewing the angle during a routine examination, it would tend to be awkward if used in a goniotomy. The design would require that the surgeon hold the lens on the eye and simultaneously perform the operation which would not be feasible. In addition the design would not be useful with a operating microscope using coaxial light.

U.S. Pat. Nos. 4,134,647, 4,378,147 and 3,820,879 all disclose various lenses useful in conjunction with the treatment of the human eye. However, these lenses are not adapted for use in conjunction with goniotomies.

SUMMARY OF THE INVENTION

It would be highly desirable to provide a lens that allows an operating microscope to be used in performing a goniotomy.

These and other objects of the present invention may be achieved by a lens useful in performing a goniotomy that comprises a truncated generally pyramidal body having four sides, a smaller end face and a larger end face. The smaller end face is concave and is adapted to conform to the human cornea. The larger end face is generally planar and is angled slightly to a perpendicular to the optical axis of the lens. The sides are reflective to enable the chamber angle to be viewed when the smaller end face is resting on the cornea.

BRIEF DESCRIPTION OF THE DRAWINGS

FIG. 1 is a partial perspective view showing one embodiment of the present invention in use on a patient's eye;

FIG. 2 is an enlarged perspective view showing the lens illustrated in FIG. 1; and FIG. 3 is a vertical cross-sectional view taken centrally through the lens generally transverse to the patient's height in FIG. 1.

DESCRIPTION OF A PREFERRED EMBODIMENT

Referring to the drawing wherein like reference characters are used for like parts throughout the several views, a goniotomy lens 10, shown in FIG. 1, may be positioned on the eyeball "A" of an upwardly facing prone patient. An operating microscope "M" may be aligned directly over the patient and the lens 10 in the patient's line of sight "O" (which is coincident with the optical axis of the lens 10) perpendicular to the horizontal plane of the patient.

The lens 10 is of a truncated generally pyramidal shape with opposed sides 12 and sides 14, 15, connected to the sides 12. The lens 10 also includes an opposed larger end face 16 and smaller end face 18. Advantageously, the aspect ratio of the lens 10, which is the ratio of its height "H" to its base width "W", indicated in FIG. 3, is less than two, and advantageously the aspect ratio is approximately 1. With this arrangement the lens has considerable stability and may be positioned on the patient's eye, normally without further support or steadying. The lens 10 may be made of any suitable transparent material used for lenses, such as glass or plastic, including Lucite, and may be of a unitary or one piece construction.

The smaller end face 18 advantageously conforms to the curvature of the human cornea "D". The end face 18 includes a planar region 20 that surrounds a spherical, concave region 22. A region 22 curvature of approximately 43 diopters has been found to be highly advantageous since with this curvature, the end face 18 creates a seal that prevents air bubbles from being trapped between the lens 10 and the eyeball. Any such air bubbles would tend to blur the view through the lens 10. The face 18 may be generally square, with a side length, indicated as "W" in FIG. 2, of about 7 millimeters. In any case the face 18 conforms to the size of an average cornea and yet leaves the limbus "F" available for insertion of the scapel (not shown).

The sides 12, 14 and 15 are angled to the optical axis "O" of the lens 10 by an angle of about 40° to about 50°. Further the sides 12, 14, 15 are suitably reflective or mirrored so that light impinging upon the sides 12, 14, 15 is reflected at the desired angle of about 48° from a horizontal plane. The sides 15 may have a height ("H") equal to about 7 millimeters.

The larger end face 16 faces upwardly with the lens self-supported on the cornea. The face 16 is angled at an angle "B" of approximately 10° to a horizontal plane "P" when the lens 10 is positioned on the eye, so that light coaxial with the optical axis of the microscope "O" is reflected slightly off axis to avoid the creation of glare. This taper is small enough not to effect the transmissive characteristics of the lens 10. Advantageously, the larger upper face 16 is generally square with a side dimension of about 14 millimeters. Because of the taper of the face 16, the sides 12 are shaped slightly differently from the sides 14 and 15. Advantageously, the area of the face 18 is about four times the area of the face 16. The larger end face 16 may be coated with a conventional non-reflective or glare resistance coating to further cut down on surface glare.

The lens 10 may be used in generally the following fashion. Initially the lens 10 is situated in a self-supporting condition on the cornea of the patient by positioning the smaller end face 18 directly on the cornea. The smaller end face 18 is sufficiently small to allow access to the limbus "F" in order to perform the goniotomy. The operating microscope "M" is then aligned with the patient's line of sight "O" and positioned at a point slightly spaced from the larger end face 16 of the lens 10. With the microscope turned on, a light source in the microscope shines coaxially with the patient's and surgeon's lines of sight. As indicated in FIG. 3, any resulting glare is reflected out of the surgeon's line of sight, as indicated at "G".

With the lends 10 in this position, the surgeon can look directly into the center of the eye by looking straight down the patient's line of sight (optical axis). By looking only slightly to either side, the surgeon can see the angle of the anterior chamber "C". This is possible because of the reflective sides 12, 14 and 15. Specifically if the surgeon's line of sight is directed towards one of the sides 12, 14 or 15, his view is reflected, as indicated at "R" to the region of the limbus or the angle of the anterior chamber, indicated at "F" in FIG. 3.

The lens 10 is highly advantageous in performing a goniotomy. Since the lens is generally self-supporting, the surgeon's hands are free to perform other functions. Because the upper face 16 is angled, the surgeon may use a standard operating microscope which has a light source coaxial with the surgeon's line of sight through the microscope. This is because the angle on the upper end face 16 reflects glare away from the surgeon's line of sight. The angle of the sides 12, 14, 15 enables the surgeon to selectively look straight into the eye or, by looking to the side, to view the angle of the anterior chamber. Moreover, the sides 12, 14, 15 are angled so that the amount of light reflected into the patient's eye is limited to a low level. Excessive light reflection can cause irritation. Finally, the curvature of the smaller end face 18 is such that the formation of air pockets between the eye and the lens 10 are minimized thereby minimizing distortions that these air bubbles would otherwise cause and eliminating the necessity of coating the eye with a jelly or other sealant.

Although the present invention has been described with respect with single preferred embodiment, those skilled in the art will appreciate a number of variations and it is intended within the appended claims to cover all such variations and modifications as come within the true spirit and scope of the present invention.

What is claimed is:

1. A lens useful in performing a goniotomy comprising a truncated generally pyramidal body having four planar sides, a smaller end face and a larger end face, said smaller end face being concave and adapted to conform to the human cornea, the larger end face, oriented in opposition to said smaller end face, being generally planar and angled slightly to a perpendicular to the optical axis of the lens, at least one of said sides being reflective and oriented to enable the chamber angle of the eye to the viewed when said smaller end face is resting on the human cornea, the ratio of the height of the lens measured along its optical axis to the width of said smaller end face being approximately one such that said lens is self-supporting atop the cornea.

2. The lens of claim 1 wherein angle of said larger end face to a perpendicular to the optical axis of the lens is approximately 10°.

3. The lens of claim 1 wherein the curvature of said smaller end face is approximately 43 diopters.

4. The lends of claim 3 wherein the diameter of the curvature of the smaller end face is approximately 7 millimeters.

5. The lens of claim 1 wherein the width of the smaller face is approximately 7 millimeters, the height of the lens is approximately 7 millimeters and the width of the larger face is approximately 14 millimeters.

6. The lens of claim 1 wherein the ratio of the area of the larger end face to the area of smaller end face is approximately 4.

7. The lens of claim 1 wherein said sides are angled at about 40° to about 50° to a horizontal plane when said lens is situated on a patient's cornea.

8. The lens of claim 7 wherein said sides are planar and are connected to one another and to said smaller and larger end faces.

9. The lens of claim 8 wherein said lens has a square horizontal cross-section.

10. The lens of claim 7 wherein said lens is made of a unitary piece of optical material.

11. The lens of claim 1 wherein said larger end face is coated with a glare-resistant coating.

* * * * *